US00PP37615P2

(12) United States Plant Patent
Kordes et al.

(10) Patent No.: US PP37,615 P2
(45) Date of Patent: Aug. 18, 2026

(54) MINIATURE ROSE PLANT NAMED 'KORpot146'

(50) Latin Name: *Rosa hybrida*
Varietal Denomination: KORpot146

(71) Applicant: W. KORDES' SÖHNE Rosenschulen GmbH & Co KG, Klein Offenseth-Sparrieshoop (DE)

(72) Inventors: Wilhelm-Alexander Kordes, Klein Offenseth-Sparrieshoop (DE); Britta Feuerhahn, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 19/465,015

(22) Filed: Jan. 30, 2026

(51) Int. Cl.
*A01H 5/02* (2018.01)

(52) U.S. Cl.
USPC ..... Plt./120

(58) Field of Classification Search
USPC ..... Plt./120
CPC ..... A01H 6/749; A01H 5/02
See application file for complete search history.

(56) References Cited

U.S. PATENT DOCUMENTS

PP27,162 P2 9/2016 Kordes
PP31,714 P2 5/2020 Kordes

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot146', is described. The new plant variety forms in abundance on a substantially continuous basis salmon-colored blossoms. The growth habit is bushy. Semi-glossy, medium green foliage is formed. Additionally, the new plant variety is particularly well suited for growing as distinctive ornamentation in the landscape.

1 Drawing Sheet

Latin name of genus and species of plant claimed: *Rosa hybrida.*

Variety denomination: 'KORpot146'.

STATEMENT REGARDING PRIOR DISCLOSURES BY THE INVENTOR

The first sale or offer for sale of the new plant variety was February 2025, on the *ROSA DANICA* website. The first sale or offer for sale of the new plant variety was by a joint inventor or another who obtained the new plant variety directly or indirectly from a joint inventor. No plants of the new variety have been sold in this country or anywhere in the world, nor has any disclosure of the new plant been made, more than one year prior the effective filing date of this application, and such sale or disclosure within one year was either derived directly or indirectly from a joint inventor.

BACKGROUND OF THE INVENTION

The new variety of miniature rose plant of the present invention was created by controlled breeding in 2021 in Offenseth-Sparrieshoop, Germany by artificial pollination wherein two parents were crossed which previously had been studied in the hope that they would contribute the desired characteristics. The female parent (i.e., the seed parent) of the new plant variety was 'KORpot085' (U.S. Plant Pat. No. 31,714). The male parent (i.e., the pollen parent) of the new plant variety was a product of the cross between an unnamed seedling (not patented) and 'KORpot050' (U.S. Plant Pat. No. 27,162).

The parentage of the new plant variety can be summarized as follows:

'KORpot085' x (unnamed seedling x 'KORpot050')

The seeds resulting from the above pollination were sown and small plants were obtained which were physically and biologically different from each other. Selective study resulted in the identification of a single plant of the new variety.

The new plant variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new plant variety are homogeneous, stable, and strictly transmissible by such asexual propagation from one generation to another. Accordingly, the new plant variety undergoes asexual propagation in a true-to-type manner.

SUMMARY OF THE INVENTION

It was found that the new variety of miniature rose plant of the present invention possesses the following combination of characteristics:

(a) abundantly and substantially continuously forming salmon-colored blossoms,
(b) exhibiting a bushy growth habit, and
(c) forming semi-glossy, medium green foliage.

The new plant variety well meets the needs of the horticultural industry. It can be grown to advantage as distinctive ornamentation in parks, gardens, public areas, and residential landscapes. Accordingly, it is particularly well suited for growing in the landscape.

The new plant variety can be readily distinguished from its ancestors. More specifically, the new plant variety displays salmon-colored flowers, whereas the 'KORpot085' variety (i.e., the seed parent) displays an orange-red colored flowers. Additionally, the new plant variety displays a pinker flower color and a solitary flower formation per stem compared to the unnamed male parent variety (i.e., the pollen parent), which displays orange-red colored flowers borne in clusters. Moreover, the new plant variety can be readily distinguished from non-parental related similar varieties. For example, the new plant variety displays salmon-colored flowers and a bushier growth habit compared to the 'KORpot029' variety (not patented) which displays orange-red colored flowers.

The new variety has been named the 'KORpot146' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new plant variety. The illustrated rose plant of the new variety was approximately twelve weeks of age and was grown indoors on its own roots in a 10.5 cm container in Klein Offenseth-Sparrieshoop, Germany on Dec. 19, 2024.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical features. The description is based on a one-year-old specimen of the new variety, observed during November 2025, while growing on its own roots in a three-gallon container in a greenhouse in Cochranville, Pennsylvania.

Botanical classification: *Rosa hybrida* cultivar 'KORpot146'.

Commercial classification: Miniature Rose.

Plant:

*Habit*.—Bushy.

*Height*.—Approximately 35.0 cm on average from the top of the soil plane.

*Width*.—Approximately 25.0 cm on average.

Branches:

*Stem color*.—Old wood: Green Group 143A. — young stems: Yellow-Green Group 144A.

*Length*.—Main stems: approximately 35.0 cm on average. — secondary stems: approximately 20.0 cm on average.

*Diameter*.—Main stems: approximately 7.0 mm on average. — secondary stems: approximately 4.0 mm on average.

*Texture*.—Smooth.

*Prickles*.—Amount: moderate; 2 to 3 prickles per internode. — young prickles: length is approximately 5.0 mm on average; width is approximately 4.0 mm on average at point of attachment; and color is Greyed-Orange Group N170A. — old prickles: length is approximately 5.0 mm on average; width is approximately 4.0 mm on average at point of attachment; and color is Greyed-Orange Group 174A.

Leaflets:

*Number*.—3, 5, and 7.

*Shape*.—Ovate; apex is acute to acuminate; and base is cuneate.

*Arrangement*.—Odd-pinnate.

*Margin*.—Serrate.

*Undulation*.—Moderate.

*Glossiness of upper side*.—Semi-glossy.

*Texture*.—Upper surface: smooth. — under surface: smooth.

*Venation pattern*.—Reticulate.

*Size*.—Terminal leaflet: length is approximately 3.7 cm on average; width is approximately 2.4 cm on average. — lower leaflets: length is typically 2.4 cm to 3.0 cm; width is typically 1.7 cm to 2.0 cm. — 5-Leaflet leaf: length is approximately 8.0 cm on average; width is approximately 5.5 cm on average.

Foliage:

*Young foliage*.—Upper surface color: Green Group 139A with a leaf margin of Greyed-Purple Group 187A with no visible venation. — under surface color: Green Group NN137D with no visible venation.

*Old foliage*.—Upper surface color: Green Group 137A with no visible venation. — under surface color: Green Group 137D with no visible venation.

*Petiole*.—Texture: upper surface is hispid; under surface is smooth. — length: approximately 1.4 cm on average. — width: approximately 1.0 mm on average. — upper surface color: Green Group 143A. — under surface color: Yellow-Green Group 144A.

*Rachis*.—Length: approximately 1.5 cm on average. — width: approximately 1.0 mm on average. — upper surface color: Green Group 143A. — under surface color: Yellow-Green Group 144A. — texture: upper surface is smooth; under surface is minutely thorny.

*Stipules*.—Length: approximately 1.2 cm on average. — width: approximately 6.0 mm on average. — margin: entire to erose. — upper surface color: Green Group 143A. — lower surface color: Green Group 143A.

Inflorescence:

*Number of flowers*.—About 12 to 15 blooms on average on a plant at once.

*Number of blossoms per stem or in a cluster*.—Typically 1 bloom per stem on average.

*Peduncle*.—Color: Yellow-Green Group 146A. — diameter: approximately 2.0 mm on average. — length: approximately 3.3 cm on average. — surface texture: hispidulous.

*Sepals*.—Number: 5. — upper surface color and texture: Green Group 143B, covered in short pubescence. — under surface color and texture: Yellow-Green Group 144A, puberulent. — size: length is approximately 2.1 cm on average; width is approximately 1.0 cm on average. — margin: entire with extensions on most sepals measuring approximately 4.0 mm in length and 1.0 mm in width on average. — shape: ovate. — apex: acute to aristate. — base: truncate as it joins the receptacle.

*Buds*.—Shape: ovoid. — size: length is approximately 2.0 cm on average; width is approximately 1.7 cm on average. — color (when opening): Red Group 39A.

*Flower*.—Form: double, cuplike. — profile: concave as it opens, and then outer petals are convex as the bloom ages and opens further. — diameter: approximately 7.0 cm on average. — height: approximately 3.0 cm on average. — duration: on the plant approximately 10 to 12 days. — petal color when first and fully opened: upper surface is Red Group 39A with a very small basal spot of Yellow Group 11A; under surface is Red Group 51A with a very small basal spot of Yellow Group 11A. — petal color at end of bloom: upper surface is Red Group 49B with no basal spot; under surface is Red Group 49C with no basal spot. — petals reflex one by one: yes.

*Fragrance*.—No noticeable scent.

*Petal*.—Number: 30 to 35 on average. — drop: good. — length: approximately 3.2 cm on average. — width: approximately 3.5 cm on average. — overall shape: broadly obovate. — margin: entire with moderate undulation. — apex shape: rounded to slightly reniform. — base shape: cuneate. — texture: upper surface is smooth; under surface is smooth.

*Petaloids*.—Number: approximately 7 on average. — length: approximately 2.0 cm on average. — width: approximately 6.0 mm on average. — color: upper surface is Red Group 39A with a very small basal spot of Yellow Group 11A; under surface is Red Group 39A with a very small basal spot of Yellow Group 11A. — texture: upper surface is smooth; under surface is smooth. — margin: entire with moderate undulation. — shape: obovate. — apex: obovate. — base: linear.

*Stamen*.—Number: approximately 178. — anthers: number is approximately 178; color is Yellow-Orange Group 19A; length is approximately 2.0 mm on average; and shape is oval. — filaments: length is approximately 4.0 mm on average and color is Yellow-Orange Group 19A.

*Pistils*.—Arrangement: separate and free. — number: approximately 80. — style: length is approximately 7.0 mm on average and color is Orange-Red Group N34C at apex and Yellow Group 8D at base. — stigma: diameter is approximately 1.0 mm on average, shape is fan shaped; color is Yellow Group 8D.

*Receptacle*.—Diameter: approximately 7.0 mm on average. — depth: approximately 7.0 mm on average. — shape: urn shaped. — color: Yellow-Green Group 144A. — surface texture: smooth.

*Pollen*.—None observed.

*Hips/seed*.—None observed.

Development:

*Vegetation*.—Semi-glossy and medium green.

*Blossoming*.—Abundant and substantially continuous from spring through frost; typically, in bloom outdoors from May to November in Southeastern Pennsylvania.

*Resistance to diseases*.—Good resistance to powdery mildew (*Podosphaera pannosa*).

*Hardiness*.—Unknown.

The new 'KORpot146' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of miniature rose plant named 'KORpot146' characterized by the following combination of characteristics:

(a) abundantly and substantially continuously forming salmon-colored blossoms, (b) exhibiting a bushy growth habit, and (c) forming semi-glossy, medium green foliage;

substantially as herein shown and described.

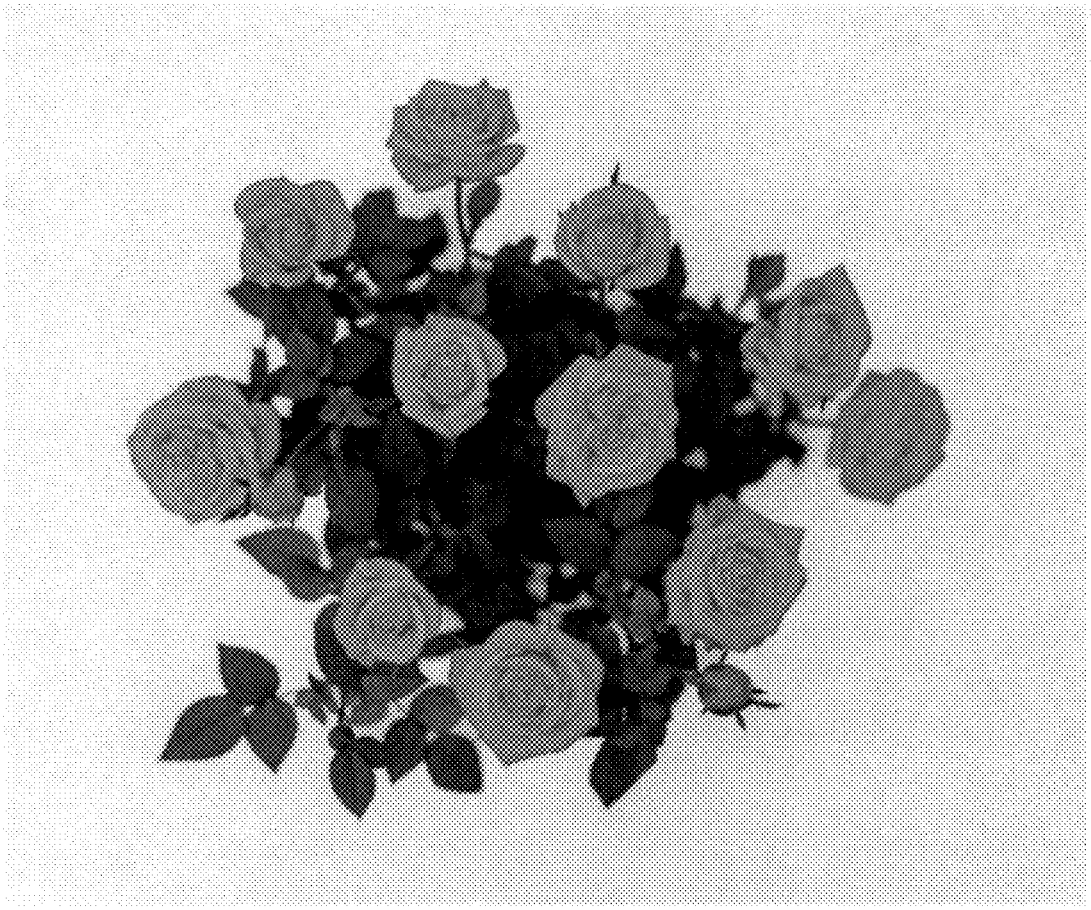

* * * * *